United States Patent [19]
Fisher et al.

[11] Patent Number: 5,800,536
[45] Date of Patent: Sep. 1, 1998

[54] PASSIVE PIEZOELECTRIC PROSTHESIS FOR THE INNER EAR

[75] Inventors: Stanley A. Fisher; Aime S. DeReggi, both of Boyds, Md.

[73] Assignee: The United States of America as represented by the Secretary of the Navy, Washington, D.C.

[21] Appl. No.: 854,032

[22] Filed: May 9, 1997

[51] Int. Cl.⁶ ............................................. A61F 2/18
[52] U.S. Cl. .................. 623/10; 607/57; 607/116; 607/137
[58] Field of Search ................. 623/10, 11, 12; 607/55, 57, 116, 137

[56] References Cited

U.S. PATENT DOCUMENTS

| | | | |
|---|---|---|---|
| 5,344,387 | 9/1994 | Lupin | 607/57 X |
| 5,649,970 | 7/1997 | Loes et al. | 607/57 |

*Primary Examiner*—Mary Beth Jones
*Attorney, Agent, or Firm*—John Forrest; Jacob Shuster

[57] ABSTRACT

A tubular prosthesis formed by an assembly of electrode segments enclosing an elongated inner chamber, is inserted into the inner ear of a patient for piezoelectric generation of electrical impulses and localized injection thereof in response to externally generated sound waves. Such electrical impulses are applied from the prosthesis to nerve endings adjacent to cochlea contact locations on the electrode segments so as to improve hearing adversely affected by biological damage to the inner ear.

8 Claims, 1 Drawing Sheet

PASSIVE PIEZOELECTRIC PROSTHESIS FOR THE INNER EAR

The present invention relates generally to a passive hearing aid positioned within the inner ear for improving impaired hearing.

BACKGROUND OF THE INVENTION

The insertion of a wide variety of prostheses into human ears in order to improve the hearing process by replacement of biologically damaged anatomical features, has heretofore been proposed for example, damage of the stapes or incus in the middle ear is overcome by a prosthesis device by restoring proper transmission of sound wave induced vibrations to the inner ear cochlea according to U.S. Pat. No. 3,711,869 to Shea, Jr. and U.S. Pat. No. 5,306,299 to Applebaum. As to the placement of a prosthesis within the cochlea itself, the use of a segmented wire having plural electrodes has already been proposed, whereby electrical impulses from the electrodes excite appropriate portions of the cochlea at nerve ending locations. Such electrical impulses are produced by current conducted to the electrodes through the segmented wire as signal processing outputs of a frequency filter device receiving sound wave inputs from an external microphone.

Some of the foregoing referred to prior art hearing aids involve relatively complex and costly equipment including active power sources such as batteries. Other types of hearing aids while being effective are expensive and involve considerable physical discomfort to the patient. It is therefore an important object of the present invention to provide a hearing aid that is effective in overcoming the effects of ear damage, in a less expensive manner and with less discomfort to the patient.

SUMMARY OF THE INVENTION

In accordance with present invention, acoustic pressurization of a passive prosthesis by sound waves, piezoelectrically generates electrical impulses internally within the inner ear to which the sound waves are transmitted from some external source without amplification or other signal processing. The prosthesis takes advantage of acoustical spatial filtering that naturally occurs within the cochlea of the ear to provide the generated electrical impulses at different frequencies which are accurately recognizable. Such prosthesis is formed from tubular electrode segments made of a piezoelectric polymer, separated by insulators and assembled into an elongated flexible tube inserted into the cochlea through the auditory canal of the ear. The flexible tube may be inflated by air pressure or a pressurized fluid applied to its inner chamber so as to establish proper contact of the radially outer electrode surfaces of the tube segments with wall membranes of the cochlea into which the internally generated electrical impulses are injected adjacent to nerve endings embedded in such membranes.

BRIEF DESCRIPTION OF THE FIGURES

A more complete appreciation of the invention and many of its attendant advantages will be readily appreciated as the same becomes better understood by reference to the following detailed description when considered in connection with the accompanying drawing wherein.

DETAILED DESCRIPTION OF PREFERRED EMBODIMENTS

Figure 1:
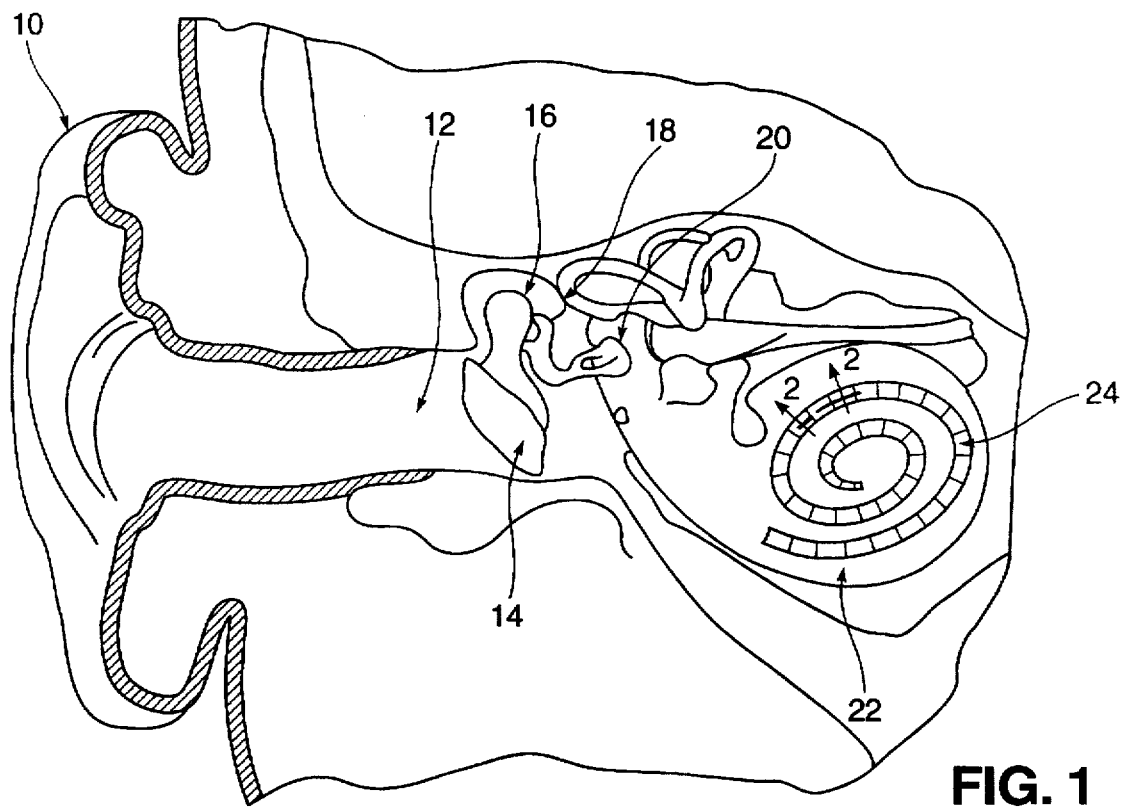
FIG. 1 is a partial section view illustrating the anatomy of a human ear within which a passive prosthesis is positioned and fitted in accordance with the present invention.

Referring now to the drawing in detail, FIG. 1 illustrates the anatomy of a human ear with which the present invention is associated, including the external ear lobe 10 leading into the auditory canal 12 through which externally generated sound waves are conducted to the middle ear cavity within which the tympanic membrane 14 is located together with the malleus 16 and the incus 18 forming a bonal chain with the stapes 20 into the cochlea 22 through which sound wave induced vibrations are transmitted. The cochlea 22 has a bony-walled cavity covered by membranes and enclosing fluids which ordinarily transmit sound wave induced vibrations to nerve endings located in the cavity wall membranes. Nerve impulses imparted to the wall membranes at spaced locations in the inner ear cavity of the cochlea 22 are relayed to the brain for conversion into perceived sound waves in connection with the human hearing phenomenon.

FIG. 1 also shows a passive prosthesis 24 having a two-dimensional snake-like shape operatively positioned in contact with the wall membranes of the cochlea cavity pursuant to the present invention. External sound wave induced vibrations transmitted to the cochlea 22 will accordingly be received by the prosthesis 24 for conversion into impulses applied to the nerve endings in the cavity wall membranes of the inner ear. Such prosthesis 24 is inserted into the cochlea 22 through the auditory canal 12 and operatively positioned as a remedial measure for improvement of hearing adversely affected by biological damage confined to the inner ear.

Figure 2:
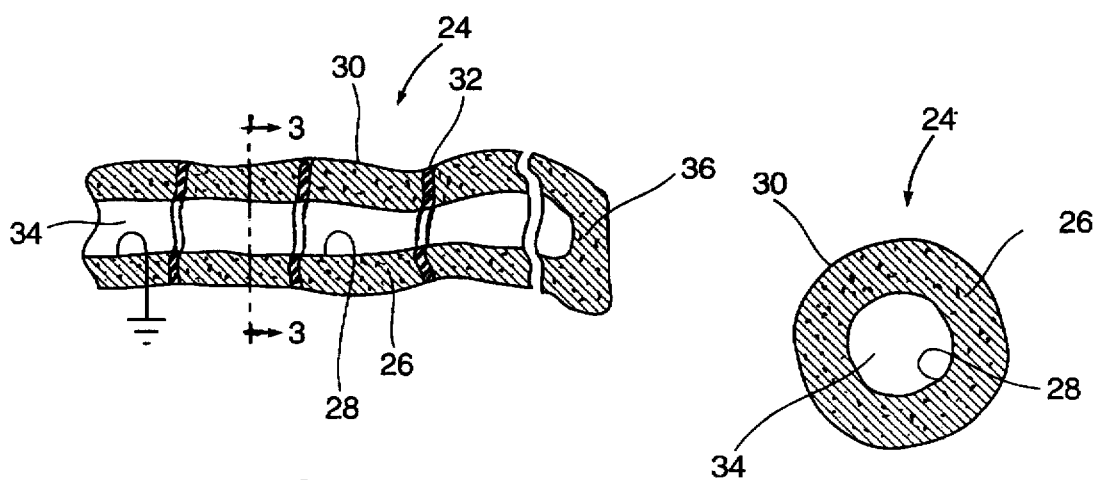
FIG. 2 is an enlarged partial section view through the prosthesis, taken substantially through a plane indicated by section line 2—2 in FIG. 1.
Figure 3:
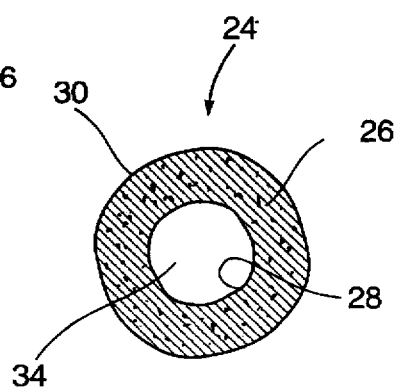
FIG. 3 is a transverse section view taken substantially through a plane indicated by section line 3—3 in FIG. 2.

Referring now to FIGS. 2 and 3, the prosthesis 24 is an elongated tubular assembly of electrode segments 26. According to one embodiment of the invention, such electrode segments 26 are made of a piezoelectric polymer material such polyvinylidene fluoride (PVDF) generally known in the art. The piezoelectric property of each segment 26 is such that pressures exerted thereon, including acoustic pressure filtered in frequency by undisturbed natural transmission of sound waves through the auditory canal and the cochlea of the human ear, will be converted into electrical current which flows between the radially inner positive electrode surface 28 to be grounded and the radially outer negative electrode surface 30 of each segment 26 from which electric impulses are emitted into the cochlea. Such segments 26 are interconnected in axially spaced relation to each other by insulating separators 32. Accordingly, the segments 26 respectively form separate electrodes within which the electrical impulses are piezoelectrically generated at a plurality of spaced locations in response to acoustic pressurization of the prosthesis 24 by acoustic pressures transmitted thereto from the auditory canal 12 and the middle ear cavity. Furthermore, the flexibility property of the segments 26 accommodates inflation of the prosthesis 24 when pressurized by air or fluid supplied to inner tube chamber 34 enclosed therein and closed at the inner end 36 of the prosthesis 24, according to the embodiment shown in FIG. 2, so as to obtain effective electrical contact between each of the electrode surfaces 30 and the spaced locations on the wall membranes of the cochlea 22 adjacent to nerve endings as aforementioned. Such inflation of the prosthesis 24 is effected after it is inserted in a contracted condition into the cochlea 22 through the auditory canal 12. The piezoelectric material selected for the prosthesis segments 26 having the properties hereinbefore referred to are in themselves already well known in the art in connection with other installational environments and usages as disclosed for example in U.S. Pat. Nos. 4,166,299, 4,405,402, 4,565,943 and 4,843,275.

It will be appreciated from the foregoing description that because of the piezoelectric generation of electrical impulses by passive reaction of the prosthesis 24 to acoustic pressurization within the cochlea 22, the use of power sources such as batteries and signal processing problems associated therewith are avoided. Also because of the selection of a flexible piezoelectric polymer as the material of the segments 24 forming the inner pressurization chamber 34, installation of the prosthesis within the inner ear with proper fit may be enhanced with less discomfort to a patient. By use of two prostheses 24, one for each of a patient's two ears, the patient may discern not only differences in frequency and sound wave levels entering the auditory canals 12 but also noise direction without any additional or external devices. Other advantages of the described prosthesis 24 include its reduced cost and complexity, increased comfort and reliability as well as easier maintenance.

In accordance with other embodiments of the present invention, the electrode segments 26 of the prosthesis 24 may be made of electret or electret-like materials such as electron or ion-implemented polymers. Other piezoelectric materials for the electrode segments 26 of the prosthesis 24 that are not elastic in nature could be used, such as piezoceramics. In such case, the insulating separators 32 would act as flexible joints between the piezo-electric segments of the elongated tube forming the prosthesis. The elongated tube would then have sufficient rigidity to hold its shape and maintain contact with the wall surfaces of the cochlea without reliance on pressurization by inflation fluid. Such form of elongated tube may therefore be open at both ends to allow circulation therethrough of natural cochlea fluids.

Obviously, other modifications and variations of the present invention may be possible in light of the foregoing teachings. It is therefore to be understood that within the scope of the appended claims the invention may be practiced otherwise than as specifically described.

What is claimed is:

1. In a method of improving hearing adversely affected by inner ear damage within a cochlea to which externally generated sound waves are transmitted through an auditory canal and tympanic membrane, including excitation of nerve endings adjacent to spaced locations in the cochlea at which electrical impulses are injected, the improvement residing in the steps of:

assembling a prosthesis subject to acoustical pressurization for piezoelectric generation of said electrical impulses; and positioning the assembled prosthesis within the cochlea for said piezoelectric generation of the electrical impulses at said spaced locations in response to said acoustical pressurization of the prosthesis internally within the cochlea by the externally generated sound waves transmitted thereto.

2. The method as defined in claim 1 wherein said step of assembling the prosthesis comprises:

formation of tubular segments of piezoelectric material; and interconnection of said tubular segments in axially spaced relation to each other by insulating separators to enclose an elongated inner chamber.

3. The method as defined in claim 2 wherein said step of positioning the assembled prosthesis comprises:

insertion of the interconnected tubular segments through the auditory canal into the cochlea; and establishing contact between the tubular segments and the cochlea at said spaced locations upon said insertion of the assembled prosthesis.

4. The method as defined in claim 3 wherein said step of establishing contact includes;

pressurizing the elongated inner chamber for inflation of the tubular segments.

5. The method as defined in claim 3 wherein said step of establishing contact includes:

formation of the tubular segments from material that is rigid relative to the insulating separators which act as flexible joints to accommodate shaping of the prosthesis for establishment of said contact.

6. In a method of improving hearing adversely affected by inner ear damage within a cochlea to which externally generated sound waves are transmitted through an auditory canal and tympanic membrane, including excitation of nerve endings adjacent to spaced locations in the cochlea at which electrical impulses are injected, the improvement residing in the steps of:

forming an assembly of tubular segments subject to acoustical pressurization for piezoelectric generation of said electrical impulses; and inserting said assembly of the tubular segments into the cochlea through the auditory canal for contact at the spaced locations from which said electrical impulses are injected in response to said acoustical pressurization by the externally generated sound waves transmitted through the auditory canal and the tympanic membrane.

7. The method as defined in claim 6 wherein said assembly of the tubular segments enclose an elongated inner chamber that is pressurized to establish said contact at the spaced locations.

8. In a method of improving hearing by application of electrical impulses to nerve endings within an ear of a patient in response to external sound waves transmitted into the ear, the improvement residing in the steps of;

assembling a plurality of spaced electrodes through which piezoelectric generation of said electrical impulses is achieved;

inserting said assembled electrodes into the ear for said piezoelectrical generation of the electrical impulses internally within the ear; and operatively positioning the inserted electrodes in contact with the ear adjacent to said nerve endings for localized injection of the electrical impulses.

* * * * *